(12) United States Patent
Nallakrishnan

(10) Patent No.: US 10,098,624 B2
(45) Date of Patent: Oct. 16, 2018

(54) SURGICAL APPARATUS AND METHOD OF USE THEREOF

(71) Applicant: Ravi Nallakrishnan Revocable Trust, Willowbrook, IL (US)

(72) Inventor: Ravi Nallakrishnan, Westmont, IL (US)

(73) Assignee: Nallakrishnan Family Trust, Willowbrook, IL (US)

( * ) Notice: Subject to any disclaimer, the term of this patent is extended or adjusted under 35 U.S.C. 154(b) by 9 days.

(21) Appl. No.: 15/336,918

(22) Filed: Oct. 28, 2016

(65) Prior Publication Data
US 2017/0049430 A1    Feb. 23, 2017

Related U.S. Application Data

(63) Continuation of application No. 14/834,049, filed on Aug. 24, 2015, now Pat. No. 9,510,814.

(60) Provisional application No. 62/186,976, filed on Jun. 30, 2015.

(51) Int. Cl.
  *A61B 1/32* (2006.01)
  *A61B 17/02* (2006.01)
  *A61F 9/00* (2006.01)

(52) U.S. Cl.
  CPC ...... *A61B 17/0231* (2013.01); *A61B 17/0293* (2013.01); *A61F 9/00* (2013.01)

(58) Field of Classification Search
  CPC .................................. A61B 17/02–17/0293
  See application file for complete search history.

(56) References Cited

U.S. PATENT DOCUMENTS

| | | | |
|---|---|---|---|
| 4,203,168 A | | 5/1980 | Rainin et al. |
| 4,321,916 A | * | 3/1982 | McKee ............... A61F 9/007 600/209 |
| 4,387,706 A | | 6/1983 | Glass |
| 4,782,820 A | | 11/1988 | Woods |
| 4,991,567 A | | 2/1991 | McCuen, II et al. |
| 5,163,419 A | | 11/1992 | Goldman |
| 5,267,553 A | * | 12/1993 | Graether ............ A61B 17/0231 600/236 |

(Continued)

FOREIGN PATENT DOCUMENTS

| | | |
|---|---|---|
| CA | 2902075 A1 | 9/2014 |
| WO | 2013059305 A1 | 4/2013 |
| WO | 2014132264 A1 | 9/2014 |

*Primary Examiner* — Jan Christopher Merene
*Assistant Examiner* — Steven Cotroneo
(74) *Attorney, Agent, or Firm* — Wood, Phillips, Katz, Clark & Mortimer

(57) ABSTRACT

A surgical apparatus for use in assisting the performance of a procedure on an eye, the eye having a front and rear, a cornea, an iris defining a pupil, and a lens capsule behind the iris. The apparatus has a frame with a front and rear, a first portion and a second portion. The frame is reconfigurable between (i) a first collapsed state for being inserted through an incision in a cornea and (ii) a second operative state for being operatively connected to an iris. The frame first portion is configured to be generally residing within a plane in the second operative state. The second frame portion is configured to be operatively connected to an iris in the second operative state exerts a pressure upon the iris at at least a first location that is spaced from the plane to maintain the pupil in an enlarged state.

14 Claims, 9 Drawing Sheets

(56) References Cited

U.S. PATENT DOCUMENTS

| | | | |
|---|---|---|---|
| 5,299,564 A | 4/1994 | Sabatino | |
| 5,322,054 A | 6/1994 | Graether | |
| 5,374,272 A * | 12/1994 | Arpa | A61B 17/0231 600/236 |
| 5,951,565 A * | 9/1999 | Freeman | A61F 2/1605 606/107 |
| 6,068,643 A * | 5/2000 | Milverton | A61B 17/0231 606/107 |
| 6,200,336 B1 | 3/2001 | Pavcnik et al. | |
| 6,231,583 B1 | 5/2001 | Lee | |
| 8,323,296 B2 | 12/2012 | Malyugin | |
| 8,439,833 B2 | 5/2013 | Christensen et al. | |
| D686,729 S | 7/2013 | Christensen et al. | |
| 8,496,583 B1 | 7/2013 | Reynard | |
| 8,852,091 B2 | 10/2014 | Sussman et al. | |
| 8,900,136 B2 | 12/2014 | Cote et al. | |
| 9,089,397 B2 * | 7/2015 | Clarke | A61F 9/007 |
| 2003/0092970 A1 | 5/2003 | Lee | |
| 2008/0108879 A1 * | 5/2008 | Brown | A61B 1/32 600/236 |
| 2008/0243139 A1 | 10/2008 | Dusek | |
| 2008/0269888 A1 * | 10/2008 | Malyugin | A61B 17/0231 623/6.42 |
| 2008/0275461 A1 * | 11/2008 | Nallakrishnan | A61F 9/007 606/107 |
| 2012/0136322 A1 * | 5/2012 | Alster | A61F 9/0017 604/290 |
| 2012/0289786 A1 | 11/2012 | Dusek | |
| 2013/0053860 A1 | 2/2013 | Malyugin | |
| 2013/0096386 A1 * | 4/2013 | Christensen | A61B 17/0231 600/206 |
| 2013/0131458 A1 * | 5/2013 | Malyugin | A61B 1/32 600/236 |
| 2013/0267988 A1 | 10/2013 | Sussman | |
| 2013/0331939 A1 * | 12/2013 | Stevens | A61F 2/16 623/6.51 |
| 2014/0221759 A1 * | 8/2014 | Mackool | A61B 17/0231 600/209 |
| 2014/0378773 A1 * | 12/2014 | Dykes | A61B 17/0293 600/208 |
| 2015/0080665 A1 | 3/2015 | Cote et al. | |
| 2015/0164685 A1 * | 6/2015 | Bhattacharjee | A61B 17/0231 606/198 |

* cited by examiner

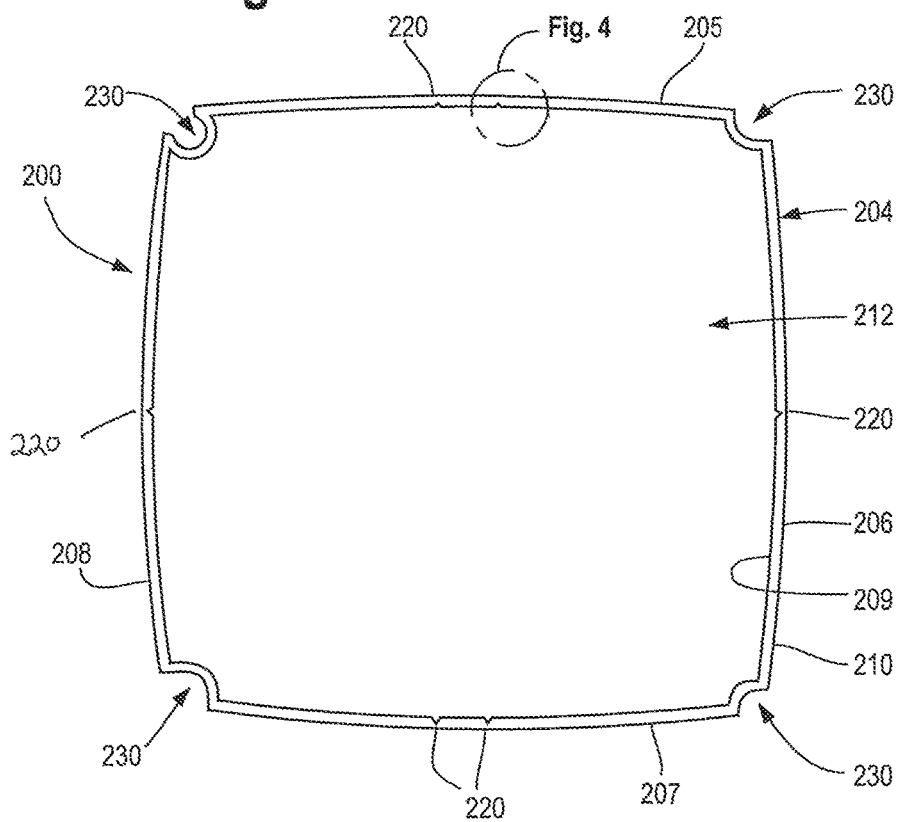
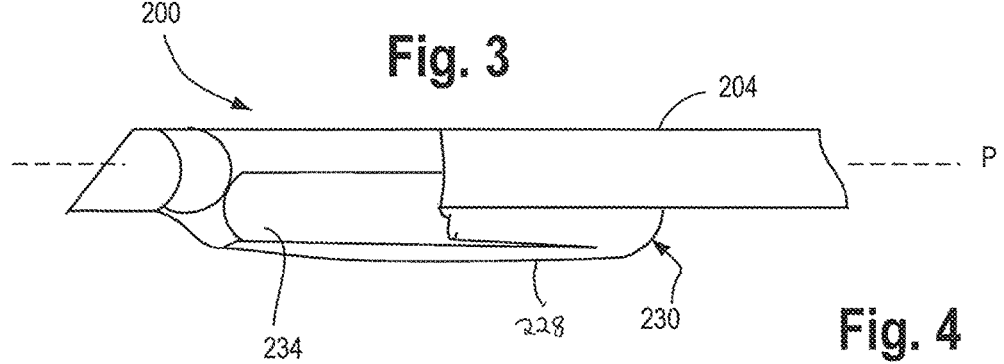
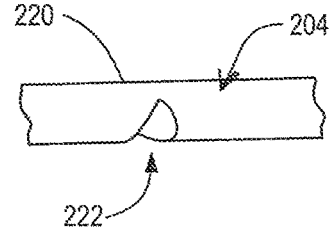

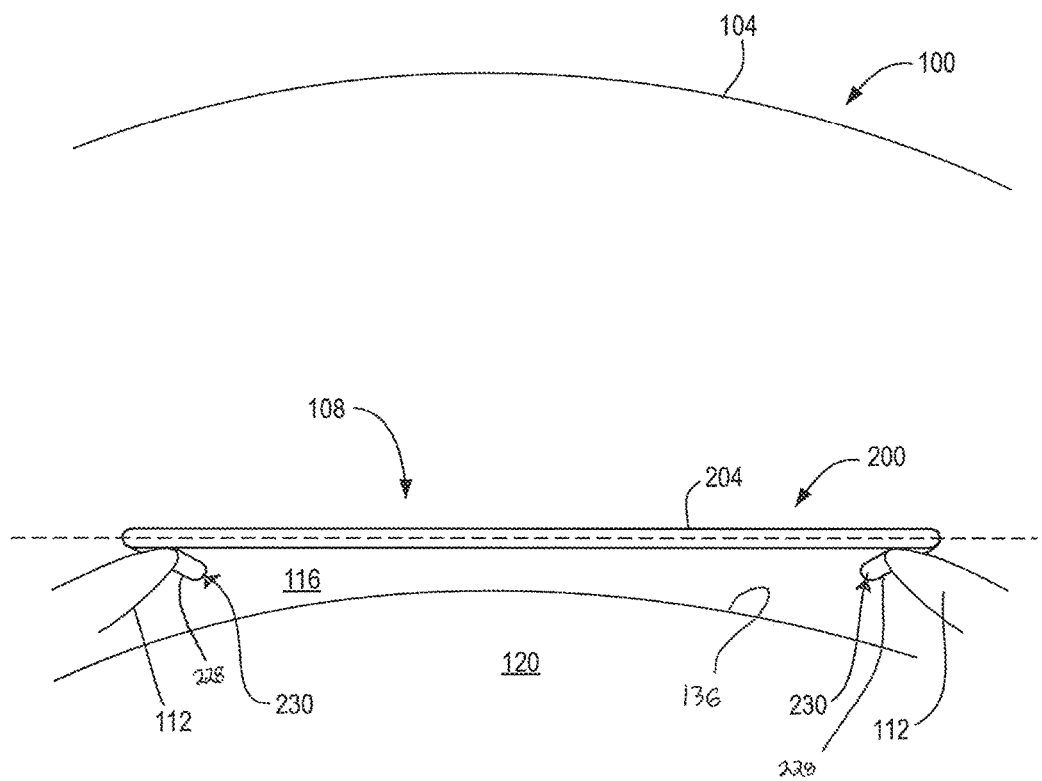

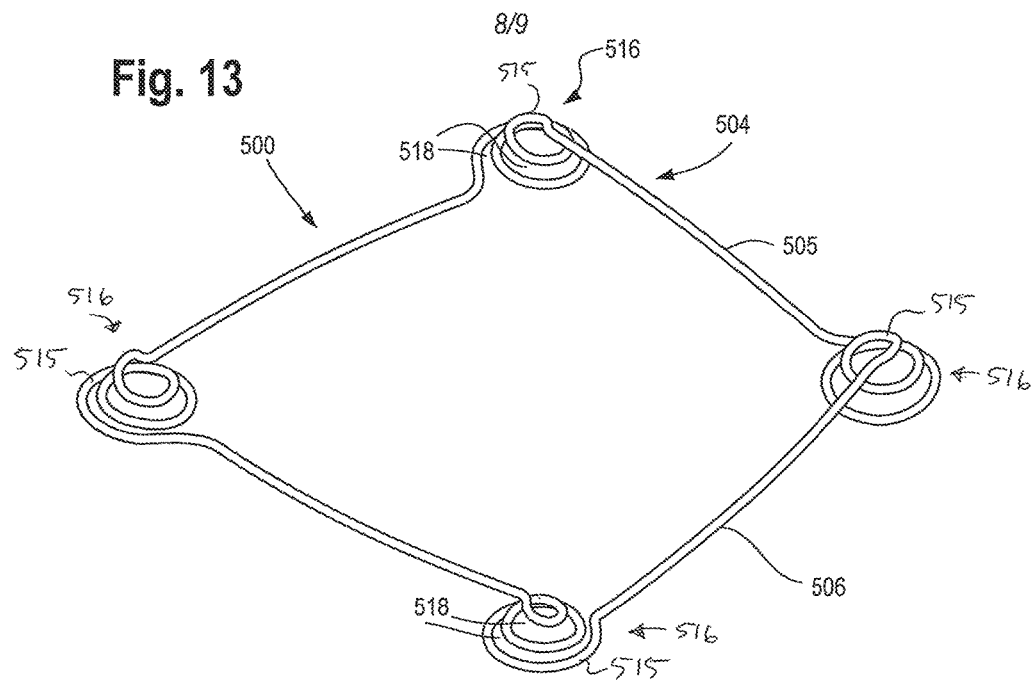
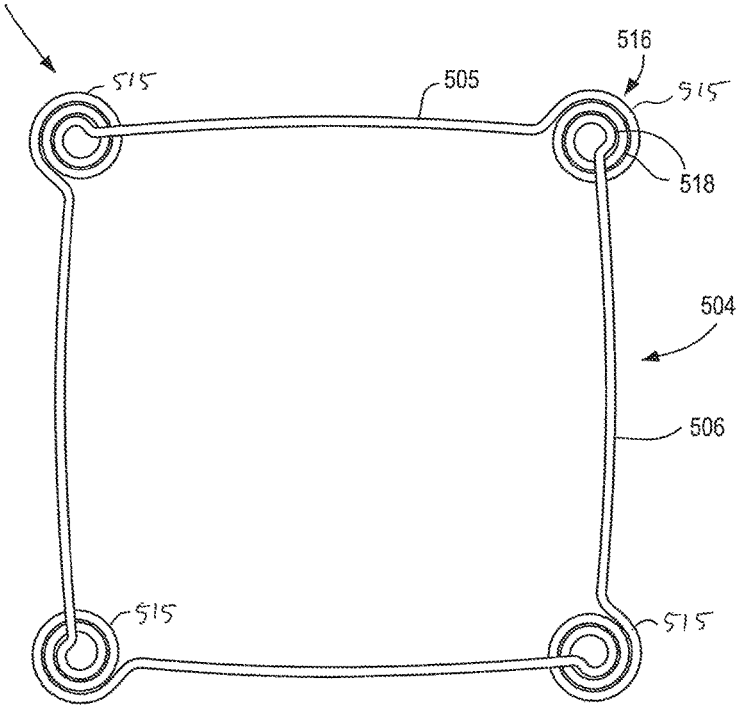

SURGICAL APPARATUS AND METHOD OF USE THEREOF

CROSS-REFERENCE TO RELATED APPLICATION(S)

This application is a continuation of U.S. patent application Ser. No. 14/834,049, filed Aug. 24, 2015, and claims priority of U.S. provisional patent application Ser. No. 62/186,976, filed Jun. 30, 2015, and those prior patent applications are incorporated here by reference in their entirety to provide continuity of disclosure, and applicant claims the benefit of those prior applications.

FIELD OF THE INVENTION

The present invention relates generally to the field of surgery, and more particularly, to an apparatus for use during ophthalmic surgery.

BACKGROUND OF THE INVENTION AND TECHNICAL PROBLEMS POSED BY THE PRIOR ART

Removal of a lens in an eye is required by such physical conditions as cataracts, disease, or trauma to the eye. Typically, the removal of the lens is accomplished by making an opening in an anterior wall of a capsule that contains the lens, and then using surgical techniques such as phacoemulsification to fragment and aspirate the fragmented lens pieces. Thereafter, an artificial intraocular lens (IOL) is inserted through the opening in the lens capsule to replace the damaged or diseased lens.

To make an opening in the lens capsule, a physician or surgeon will first retract the iris, thus dilating the pupil, to provide an adequate exposure of the lens capsule. This may be typically done through chemical dilation of the iris. However, for some patients a mechanical iris retractor must be utilized to retract or pressure the leading edges of the iris. This might be done in the case of a small or damaged iris or where chemical dilation is otherwise inappropriate. The mechanical iris retractor may be a simple elongate rod with a hook, which may be placed through an incision in the cornea and located to pull back the iris. Multiple hooks would need to be used to provide an adequate operating space or aperture within which to work. Alternatively, some retractors form a continuous frame and may be collapsed for being injected through an incision in the cornea and then resiliently expanded within the anterior chamber of the eye. Once the iris is retracted and the anterior capsule wall is adequately exposed within a window or aperture of the iris retractor, the surgeon will use surgical instruments such as forceps or a needle to puncture the anterior capsular wall, then grip the wall at the site of the puncture and tug or tear the wall, preferably in a circular pattern to remove a portion of the wall large enough and appropriately shaped to receive an artificial IOL.

The above-discussed procedure requires significant skill on the part of the surgeon. It is not uncommon for the delicate tissues of the iris to become functionally and cosmetically damaged by over-tensioning or over-pressurizing by mechanical retraction. Further, some prior art mechanical retractors only have a single size or mode of operation. For some hook-like mechanical retractors, several incisions must be made in a cornea in addition to time consuming manual adjustments of the hook tension.

It would be desirable to provide an improved surgical apparatus wherein the above-discussed problems could be eliminated, or at least substantially minimized.

It would further be desirable to provide an improved iris retractor that may be utilized for a variety of patients having differing pupil sizes or iris health.

It would also be desirable to provide an improved iris retractor that could quickly be reconfigured or adjusted to provide a variable pressure in-situ within the eye.

Further, it would be beneficial if such an improved iris retractor could be manufactured without incurring excessive costs or expenses.

SUMMARY OF THE INVENTION

The inventor of the present invention has determined how to provide an inventive surgical apparatus for use in assisting the performance of a procedure on an eye, the eye having a front and a rear, a cornea, an iris defining a pupil, and a lens capsule behind the iris. In one form, the apparatus has a frame with a front and a rear, a first portion and a second portion. The frame is reconfigurable between (i) a first collapsed state for being inserted through an incision in a cornea and (ii) a second operative state for being operatively connected to an iris. The frame first portion is configured to be generally residing within a plane in the second operative state. The second frame portion is configured to be operatively connected to an iris in the second operative state to exert a pressure upon the iris at at least a first location that is spaced from the plane to maintain the pupil in an enlarged state.

BRIEF DESCRIPTION OF THE DRAWINGS

In the accompanying drawings forming part of the specification, in which like numerals are employed to designate like parts throughout the same:

FIG. 2 is top view of a first embodiment of an apparatus according to the present invention;

FIG. 3 is an enlarged, partial, detailed view of a portion of the apparatus shown in FIG. 2;

FIG. 4 is another enlarged, partial, detailed view of a portion of the apparatus shown in FIG. 2;

FIG. 5 is a diagrammatic view of the apparatus shown in FIG. 2 operatively engaged with the human eye;

FIG. 13 is a perspective view of another embodiment of an apparatus according to the present invention;

FIG. 14 is a top plan view of the apparatus shown in FIG. 13; and

DETAILED DESCRIPTION OF THE DRAWINGS

While the following describes a preferred embodiment or embodiments of the present invention, it is to be understood that this description is made by way of example only and is not intended to limit the scope of the present invention. It is expected that alterations and further modifications, as well as other and further applications of the principles of the present invention will occur to others skilled in the art to which the invention relates and, while differing from the foregoing, remain within the spirit and scope of the invention as herein described and claimed.

Figure 1:
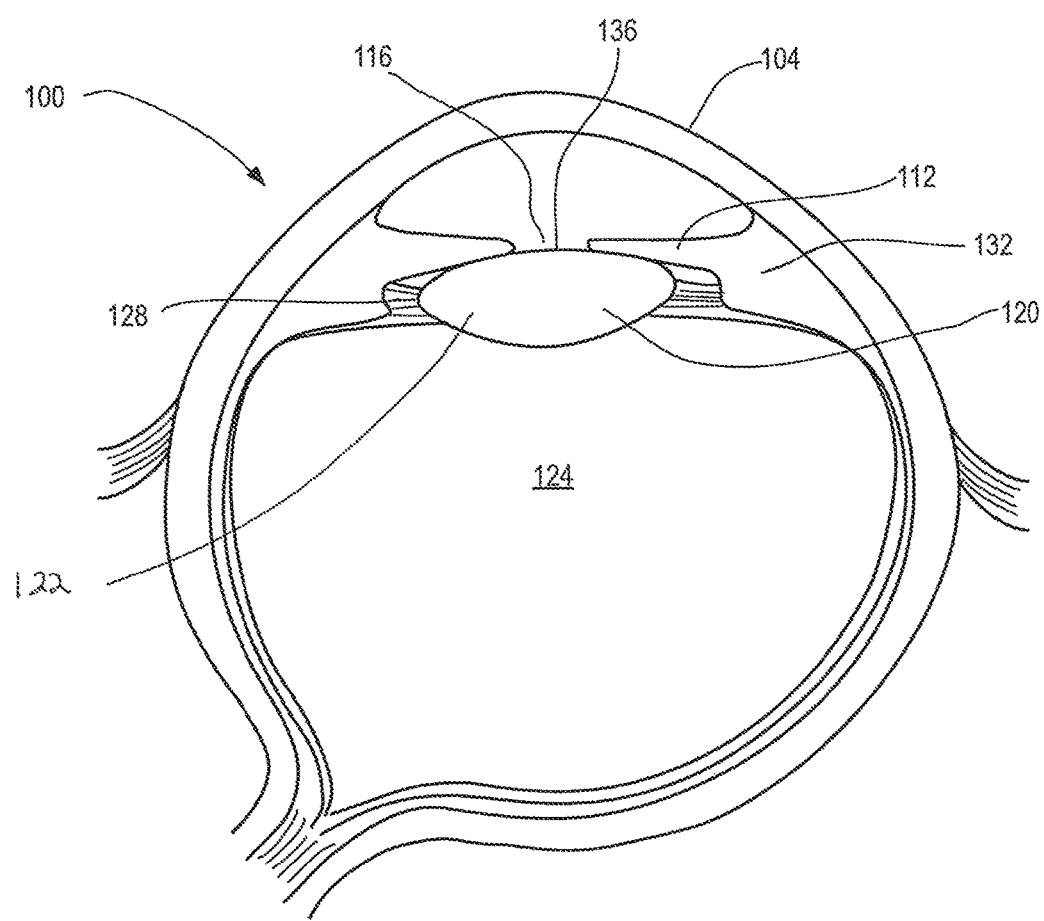
FIG. 1 is a diagrammatic, front-to-rear cross-sectional view through the center of a human eye.

Referring to FIG. 1, the numeral 100 identifies a diagrammatic, cross-sectional view taken generally through the center of a human eye showing the cornea 104, iris 112 and pupil 116. Positioned behind the iris 112, and in line with the pupil 116, is the capsular bag 120, within which the natural lens 122 resides. A posterior chamber 124 is rearward or behind the capsular bag 120. A ciliary body 128 helps support capsular bag 120 through fiber-like zonules 132. Directions as utilized herein are made with reference to the eye 100. Outwardly or forwardly refers to the general direction moving from the posterior or rear portions of the eye (e.g., the posterior chamber 124) toward the anterior or front portions of the eye (e.g., the cornea 104).

Typically, when performing capsulorhexis, a surgeon creates an incision in the cornea 104 through which forceps or a needle is inserted and used to pierce the anterior portion or wall 136 of capsular bag 120 and to shear or tear it in a circular pattern to allow the damaged or diseased lens to be removed by phacoemulsification and, thereafter, the insertion of an IOL into capsular bag 120. To assist with performing capsulorhexis, the pupil is dilated by mechanically retracting the iris 112. Known methods for mechanically retracting the iris 112 involve insertion of collapsed structures through the incision in the cornea 104, which are subsequently expanded into a deployed configuration whereby the iris 112 is pulled back from the center of the eye and the pupil 116 is dilated. Upon the removal of the anterior portion 136 of the capsule 120, the deployed structure may be re-collapsed and pulled from the eye through the incision in the cornea 104.

Figure 6:
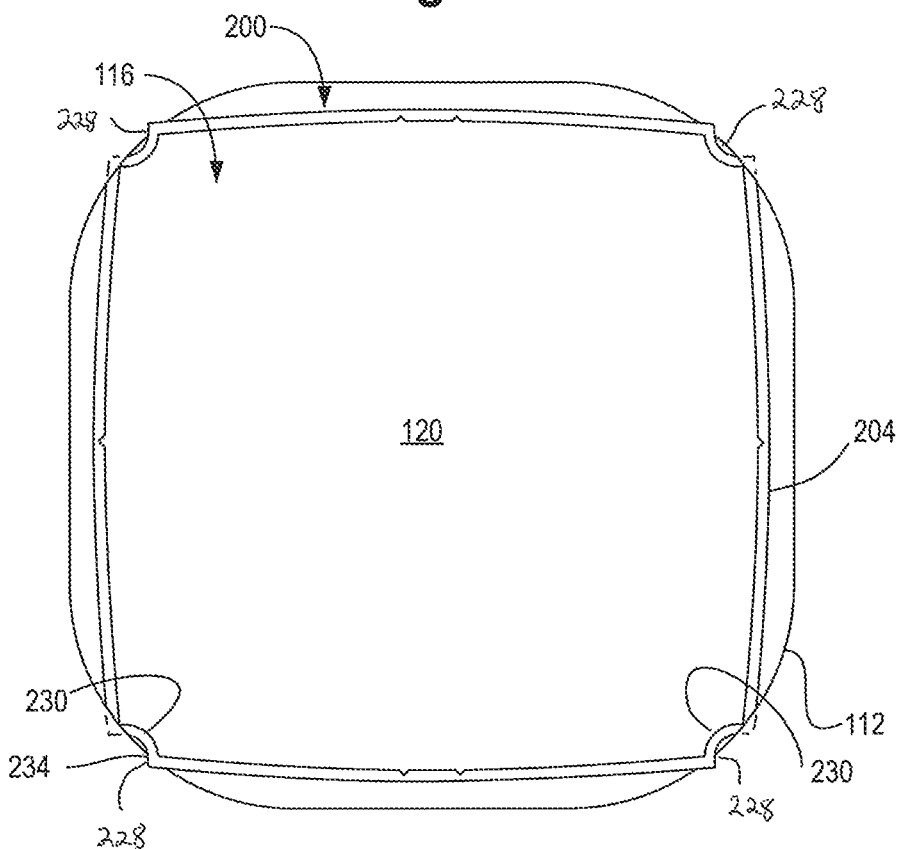
FIG. 6 is a top plan view of the apparatus shown in FIG. 2 operatively engaged with the human eye.

Referring now to FIGS. 2-7, a first embodiment of a surgical apparatus, pupil expander, iris retractor, or simply retractor according to the present invention is denoted by numeral 200. The retractor 200 is made up of a frame that has a first state in which it is collapsed. In FIG. 2, the retractor/frame 200 is generally shown in a deployed or second operative state that the retractor 200 may have within the pupil 116 (FIGS. 5 and 6) so as to operatively connect with, and retract, the iris 112 (FIGS. 5 and 6). The retractor collapses into the first starting state and can be inserted through an incision in the cornea 104 (FIG. 1), as will be discussed in detail hereinafter. The retractor 200 is preferably injection molded or otherwise formed from a resilient material such as molded silicone, nylon, polypropylene, acrylic or polymethyl methacrylate (PMMA), wire, coated wire, etc. that may be collapsed for insertion through a small incision in the cornea 104, and which resiliently expands thereafter with sufficient rigidity to mechanically retract the iris 112. Various features of the retractor/frame 200 may be punch cut, molded, photoetched, etc.

Referring to FIG. 2, the retractor/frame 200 has a resilient first frame portion 204 that forms a closed loop with a generally polygonal shape. The first frame portion 204 may have a variety of shapes, such as circular, a three-sided polygon, a polygon with more than four sides, or an irregular or curved loop etc., but is preferably rectangular and defines four segments or sides 205, 206, 207, and 208. As will be discussed in detail hereinafter, in the second operative state, the first frame portion 204 generally resides in a horizontal plane P running therethrough (FIG. 3). The term "lateral", as used hereinafter, refers to directions generally within the plane P, while the terms "front" and "rear", as used hereinafter, refer to the two directions running transversely to the plane P.

As best seen in FIG. 2, the first frame portion 204 has a laterally inward surface 209 and a laterally outward surface 210. The laterally inward surface 209 defines a window or aperture 212 that provides, in the second operative state, an unobstructed area within which the physician may operate with various surgical instruments. The first frame portion 204 is formed from a generally cylindrical tube and has a generally circular cross-section taken normal to the plane P, but it will be understood that the first frame portion 204 may have a square, or anther polygonal or irregular cross-sectional shape.

With reference to FIG. 4, the first frame portion 204 may be provided with a plurality of thinned regions, defining living hinges, or simply hinges 220. Each of the depicted hinges 220 is defined by a notch 222 in the first frame portion 204 to assist in bending of the iris retractor 200 in a predetermined manner into a collapsed configuration. As illustrated in FIG. 2, the retractor 200 is depicted as having six hinges 220 located on the first frame portion 204; four hinges 220 are located on sides 205 and 207 of the frame 204, while two hinges 220 are located on the other sides 206 and 208 of the first frame portion 204. The hinges 220 are preferably located on the first frame portion 204 such that the notches 222 are located on the interior or laterally inward surface 209 to assist in the bending of the first frame portion 204 generally within the plane P. It will be appreciated that the first frame portion 204 may be provided without any hinges 220 or the hinges 220 may be located, oriented, or spaced differently on the first frame portion 204 to assist in other modes of collapsing, expanding, folding, or unfolding.

Referring to FIG. 6, extending from the first frame portion 204 are four iris engagement members 228 collectively making up a second frame portion 230. Each iris engagement member is configured to accommodate or receive a leading edge portion of the iris 112 as discussed hereinafter. Each engagement member 228 has an abutment surface 234 (FIGS. 3 and 6) that defines a recess or channel that may receive the iris 112 to operatively connect the retractor/frame 200 with the iris 112. The shape of each engagement member 228 depicted is generally arcuate, and can be characterized as a laterally open loop or a horseshoe when viewed from a point rearward or forward of the plane P. However, it will be understood that the first frame portion 204 may have any number of engagement members 228 for engaging the iris 112, and each engagement member 228 may have other shapes such as laterally outwardly extending arms or projections, laterally inwardly extending projections, loops, coils, or any series of bends defining spaces and abutment surfaces for receiving a portion of the iris 112, as will be discussed in detail hereinafter.

Referring to FIG. 3, each engagement member 228 extends rearwardly out of the plane P defined by the first frame portion 204. It is believed that operatively connecting the iris 112 (FIG. 5) at at least one location outside of the plane P will result in a localized torsion on the leading edge of the iris 112, which in turn may enhance the connection between the iris retractor 200 and the iris 112. It will be appreciated that in some applications one, some, or all of the engagement members 228, making up a second frame portion, shown schematically as 230' (FIG. 7) may extend forwardly of the plane P so as to operatively connect with the iris 112 at at least one location that is substantially forward of the plane P. Still in other applications, one or more of the engagement members 228 may extend rearwardly to engage the iris 112, while one or more other engagement members 228 may extend forwardly to engage the iris 112. In such configurations, the arrangement of the engagement members 228 would extend from the first frame portion 204, so as to distribute the forces symmetrically between the iris 112 and the retractor/frame 200.

Operation of the retractor 200 will now be discussed. The retractor 200 is preferably manufactured or otherwise formed such that the first frame portion 204 resides within the plane P, and each engagement member 228 extends substantially outside of the plane P. The retractor/frame 200 may be manually bent or collapsed by a surgical instrument such as forceps, or the retractor/frame 200 may be collapsed and loaded into a cannula or needle of a plunger-type injector. The folded or compressed state of the retractor/frame 200 represents a first starting state. It is a well-known ophthalmic surgical technique to fold iris retractors or IOLs to decrease their size to thereby minimize the size of the incision which must be made through the cornea 104 (FIG. 1) to allow the iris retractor or IOL to be inserted therethrough. The flexible material of the retractor/frame 200, and the inclusion of the hinges 220, aid the retractor/frame 200 in collapsing so as to fit within an injector needle and through the incision in the cornea 104. If the use of an injector is not desirable, then the retractor/frame 200 may be folded or stored within a blister-type package or case and removed with forceps. Preferably, Kelman-McPherson style grooved forceps or straight forceps with a 15-deg curve could be utilized.

Referring to FIGS. 5 and 6, after an incision has been made through the cornea 104 (FIG. 5), such as by a knife or scalpel, the folded or collapsed retractor/frame 200 is injected or inserted through the incision and positioned within anterior chamber 108 (FIG. 5). The surgeon then positions the first frame portion 204 within the pupil 116 such that a lead edge portion of the iris 112 is encased by each engagement member 228. Specifically, the iris 112 is placed within each channel of each engagement member 228 to contact each abutment surface 234 (FIG. 5). The surgeon then positions one portion of each abutment surface 234 forward of the iris 112 and the other portion of each abutment surface 234 rearward of the iris 112 to exert a pressure against the iris 112 and to locate the retractor/frame 200 generally in the center of the expanded pupil 116. The pressure of each abutment surface 234 occurs at at least one location that is spaced rearward of the plane P.

In this second operative state, the retractor 200 provides sufficient pressure against the leading edges of the iris 112 so as to safely expand the pupil 116 without damaging the delicate tissues of the iris 112. Expansion of the pupil 116 provides the aperture 212 within which the physician will operate with various surgical instruments such as a needle for performing the capsulorhexis, phacoemulsification and aspiration, etc.

After surgery on the capsular bag 120 has been completed, each engagement member 228 may be sequentially operatively disengaged from the iris 112. The disengagement of the iris 112 from within each channel of each engagement member 228 removes the pressure on the leading edges of the iris 112 and the retractor/frame 200 is pulled forwardly of the iris 112. Thereafter, the retractor/frame 200 may be collapsed by forceps, into the first starting state, and pulled through the corneal incision and removed from the eye 100.

It will be appreciated that the retractor/frame 200 could alternatively be manufactured such that the first frame portion 204 and the second frame portion 230 both generally reside within plane P. In such a configuration, when each engagement member 228 engages the iris 112, it will move or bend rearwardly of the first frame portion 204 under the pressure of the iris 112 with the retractor/frame 200 in the second operative state. After each engagement member 228 is disengaged from the iris 112, then the second frame portion 230 would then return to reside within the plane P due to the resiliency of the material of the retractor/frame 200. Such a configuration may be more easily and cheaply manufactured, and further may fit more easily through the incision in the cornea 104.

It will be appreciated that while various theories and explanations have been set forth herein with respect to how the frame portions of the retractor operate, there is no intention to be bound by such theories and explanations. Further it is intended that all structures falling within the scope of the appended claims are not to be otherwise excluded from the scope of the claims merely because the operation of such structures may not be accounted for by the explanations and theories presented herein.

Figure 7:
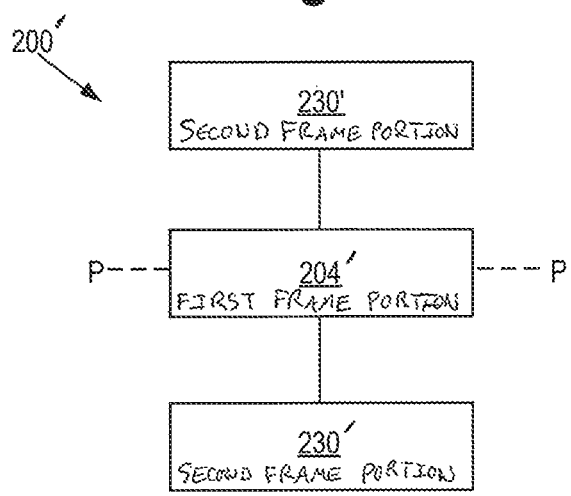
FIG. 7 is a diagrammatic view of an apparatus according to the present invention.

Referring to FIG. 7, in a schematic depiction of the present invention, the iris retractor/frame 200' has the basic components of a first frame portion 204' that generally resides within a plane P and one or more engagement members making up a second frame portion 230' that extends substantially out of the plane P when the retractor/frame 200' is in the second operative state. Part of the second frame portion 230' may extend rearward of the plane P, and/or part of the second frame portion 230' may extend forward of the plane P. Variation of the location at which the iris 112 contacts the second frame portions 230/230' (at at least a location that is forward and/or rearward of the plane P of the first frame portion 204) allows for different pressures or localized torsional effects on the iris 112. Such changes of the pressures and torsions on the iris may be desirably made quickly by the surgeon, in situ within the eye. The schematic depiction is intended to encompass not only the specific embodiments described herein, but variations thereof including virtually an unlimited number of variations of the components making up the retractor/frame 200' and their interaction.

Figure 8:
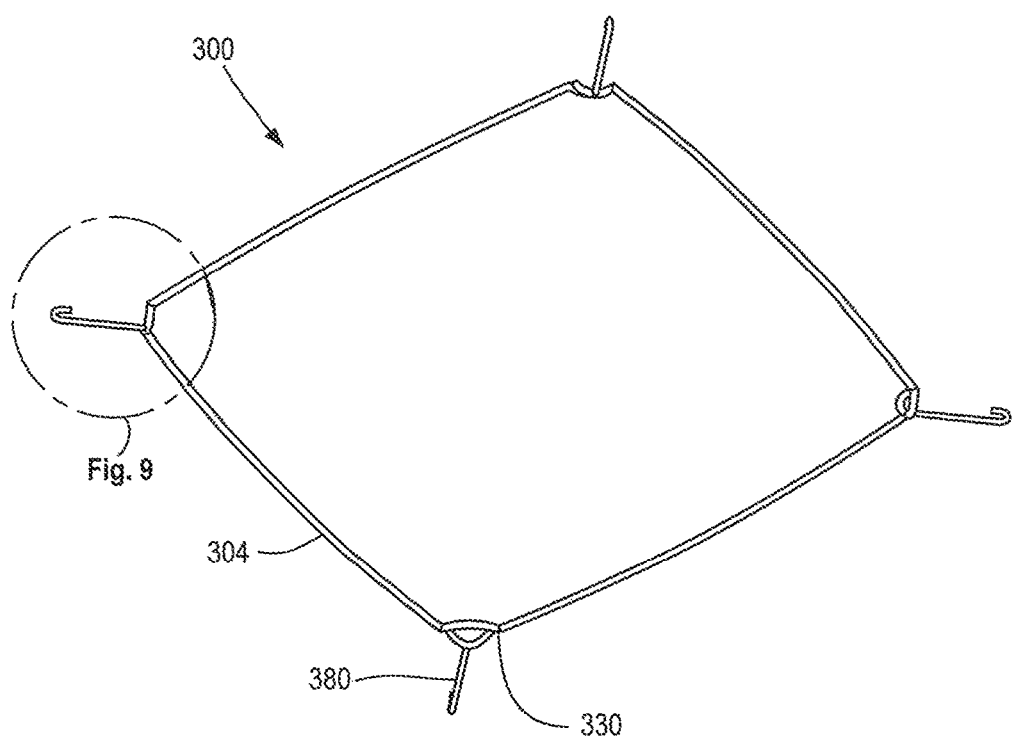
FIG. 8 is a perspective view of another embodiment of an apparatus according to the present invention.
Figure 9:
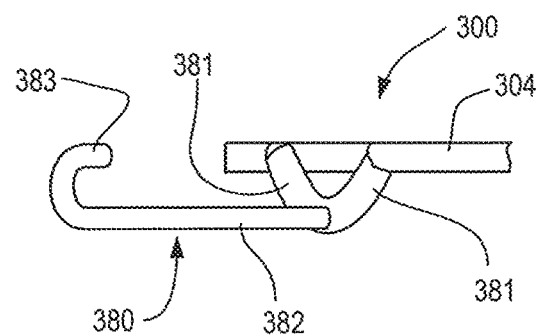
FIG. 9 is a partial, detailed view of a portion of the apparatus shown in FIG. 8.
Figure 10:
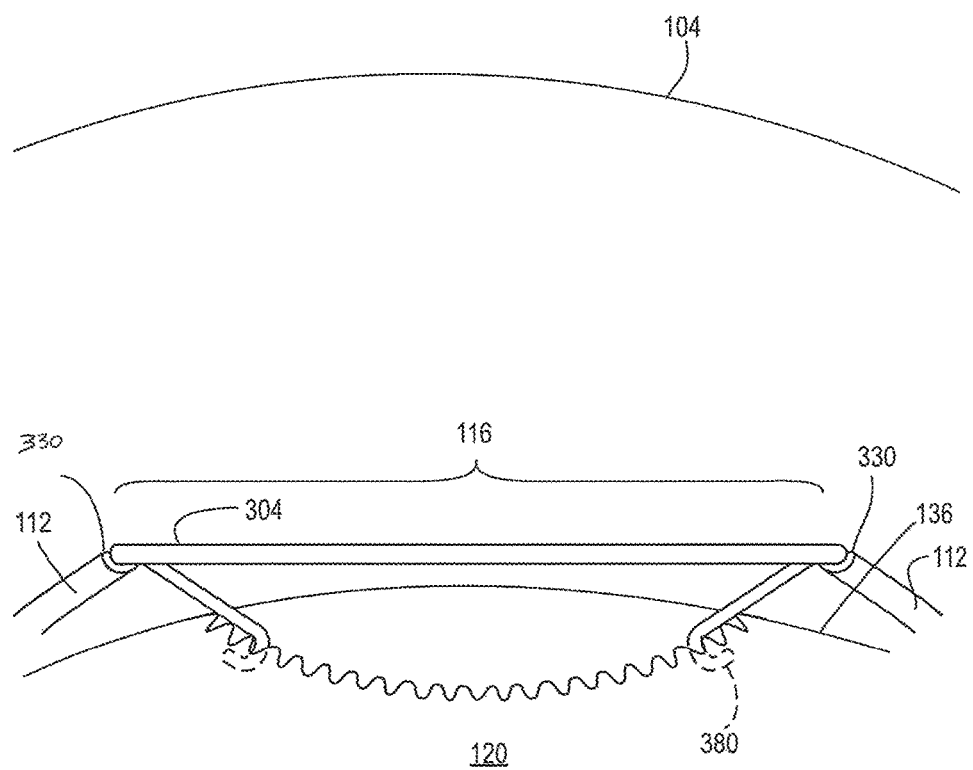
FIG. 10 is a diagrammatic view of the apparatus shown in FIG. 8 operatively engaged with the human eye.

Referring next to FIGS. 8-10, another embodiment of the inventive iris retractor is illustrated and referenced by the numeral 300. The retractor 300 functions in substantially the same manner as the retractor 200, in that the retractor 300 has a first frame portion 304 and a second frame portion 330 for being operatively connected with the iris 112 (FIG. 10) at at least one location spaced from of a plane in which the first frame portion 304 resides. The retractor 300 differs in that it has a plurality of projections, hooks, or capsule engagement members 380 extending from the first frame portion 304 and defining a second frame portion 330. The capsule engagement members 380 serve to engage or lift the capsule 120 (FIG. 10) in the anterior or forward direction after the capsulorhexis has been performed so as to stabilize the capsule 120 prior to, or during, phacoemulsification of the lens. The capsule engagement members 380 are preferably formed to reside generally adjacent the plane P in the as-manufactured state, and then may be urged away the first frame portion 304 when the first frame portion 304 is pressured by the iris 112 to place the retractor/frame 300 in the second operative state as seen in FIG. 10. The capsule engagement members 380 preferably have the form of a pair of short legs 381 (FIG. 9) that join at a central, elongate body 382 (FIG. 9) that terminates in a generally U-shaped hook 383 (FIG. 9). It will be appreciated that the capsule engagement members 380 may terminate in other configurations such as discrete projections, or loops having a polygonal, circular, or an irregular shape.

Figure 11:
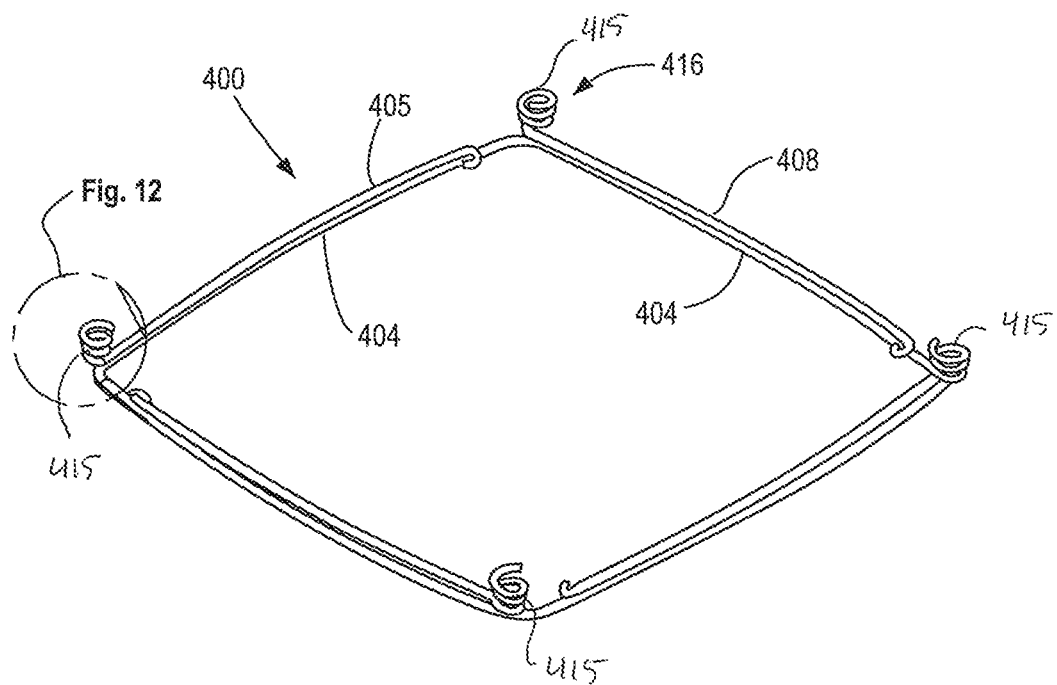
FIG. 11 is a perspective view of another embodiment of an apparatus according to the present invention.
Figure 12:
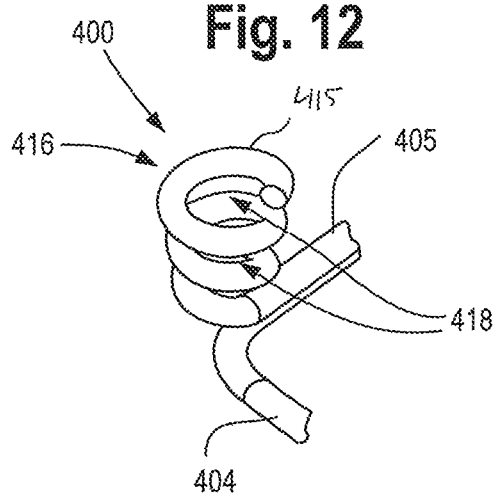
FIG. 12 is an enlarged, partial, detailed view of a portion of the apparatus shown in FIG. 11.

Referring next to FIGS. 11 and 12, another embodiment of the inventive iris retractor/frame is illustrated and referenced by the numeral 400. The retractor/frame 400 functions in substantially the same manner as the retractor/frame 200, in that the retractor/frame 400 has a first frame portion 404 generally residing within a plane with the retractor/frame 400 in the second operative state, and a plurality of iris engagement portions 415 together defining a second frame portion 416 for accommodating or receiving the iris 112 (not shown in FIGS. 11 and 12) at at least one location spaced from the plane. However, the retractor/frame 400 differs in that each engagement portion 415 has the form of an expanding spiral which defines a plurality of channels 418 that are spaced along a front-to-rear axis, and each of which is configured for receiving a portion of the iris 112. The surgeon may select the particular channels 418 within which to accommodate the leading edge of the iris 112, and the selection of different channels 418 that are spaced along a front-to-rear axis allows the physician to alter the effective diameter (the distance between corresponding channels of two engagement portion 415) of the retractor/frame 400. Increasing the effective diameter of the retractor 400 will decrease the pressure exerted upon the iris 112, and decreasing the effective diameter of the retractor/frame 400 will increase the pressure exerted upon the iris 112. The inventor has found that it would be desirable to provide the physician with a means to alter the effective diameter of, and vary the pressure exerted by, the retractor/frame 400 in situ within the eye. In this manner, a single retractor/frame 400 may be used for a variety of pupil sizes and iris conditions instead of the physician needing to pre-select the appropriate retractor prior to, or during, surgery.

Referring to FIG. 12, the first frame portion 404 differs from the first frame portion 204 in that the first frame portion 404 is provided with a tension bar or arm 405. The arm 405 serves as a damping or lost motion structure for reducing the pressures exerted on the delicate iris 112 tissues. As can be seen FIG. 11, the arm 405 has a first end connected to and extending from the first frame portion 404 and a cantilevered or free end that terminates at tot second frame portion 416. The length of the arm 405 could be altered to provide different amounts of lost motion. In the broad concept of the invention, it will be understood that the retractor/frame 400 may be provided without one of: (i) the arm 405; or (ii) the spiraled engagement portions 415, depending on the need of the particular patient and/or the preference of the physician.

Referring next to FIGS. 13 and 14, another embodiment of the inventive iris retractor/frame is illustrated and referenced by the numeral 500. The iris retractor/frame 500 functions in substantially the same manner as the retractor/frame 400, in that the retractor/frame 500 has a first frame portion 504 having a center of mass that generally resides within a plane, and a plurality of iris engagement portions 515 together making up a second frame portion 516 for accommodating or receiving the iris 112 (not shown in FIGS. 13 and 14) at at least one location spaced from the plane. The retractor/frame 500 is likewise similar in that each engagement portion 515 has the form of a spiral which defines a plurality of channels 518 that are spaced generally along a front-to-rear axis, and each of which is configured for receiving a portion of the iris 112. In use, the surgeon may select the channels 518 within which to accommodate the leading edge of the iris 112, and the selection of different channels 518 that are spaced along a front-to-rear axis allows the physician to alter the effective diameter (the distance between corresponding channels of two engagement portions 515) of the retractor/frame 500. Increasing the effective diameter of the retractor/frame 500 will decrease the pressure exerted upon the iris 112, and decreasing the effective diameter of the retractor/frame 500 will increase the pressure exerted upon the iris 112. The inventor has found that it would be desirable to provide the surgeon with a means to alter the effective diameter of, and vary the pressure exerted by, the retractor/frame 500 in situ within the eye. In this manner, a single retractor/frame 500 may be used for a variety of pupil sizes and iris conditions instead of the surgeon needing to pre-select the appropriate retractor prior to, or during, surgery.

The retractor/frame 500 differs from the preceding retractor/frame 400 primarily in that the retractor/frame 500 has a first side portion 505 that has (i) a first end terminating at the smallest (top) part of one spiraled engagement portion 515, and (ii) a second end terminating at the largest part (bottom) of another spiraled engagement portion 515. In this manner, the retractor/frame 500 may be more easily manufactured and may have an improved structural stability when compared to the preceding retractor/frame 400. Furthermore, the location at which the retractor/frame 500 operatively engages the iris 112 may be altered in situ without the entire retractor/frame 500 having to be flipped about the central plane, as would be required in the retractor/frame 400.

Figure 15:
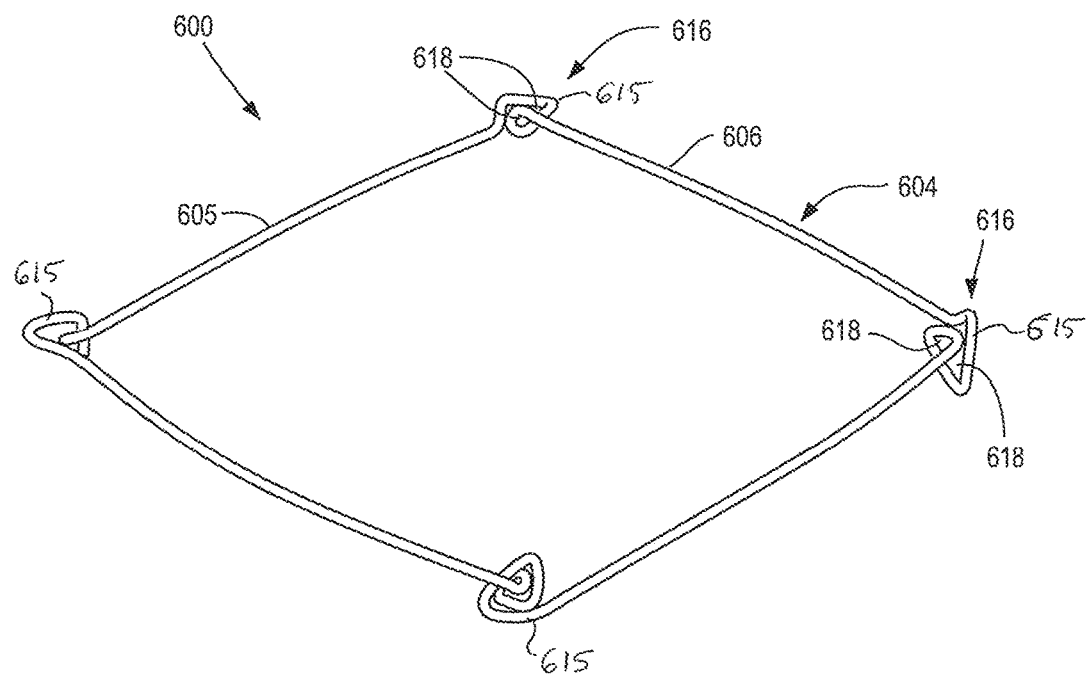
FIG. 15 is a perspective view of another embodiment of an apparatus according to the present invention.

Referring to FIG. 15, another embodiment of the inventive iris retractor/frame is illustrated and referenced by the numeral 600. The retractor/frame 600 functions substantially the same as the retractor/frame 500, in that the retractor/frame 600 has a first frame portion 604 with a center of mass that generally resides within a plane, and a plurality of iris engagement portions 615 together defining a second frame portion 616 for accommodating or receiving the iris 112 (not shown in FIG. 15) at at least one location spaced from the plane. The retractor 600 is likewise similar in that each engagement portion 615 defines a plurality of channels 618 that are spaced along a front-to-rear axis, and each of which is configured for receiving a portion of the iris 112. The retractor/frame 600 differs primarily in that the shape of each second frame portion 616 is a polygonal or triangular coil or spiral.

The invention claimed is:

1. A surgical apparatus for use in assisting the performance of a procedure on an eye, the eye having a front and a rear, a cornea, an iris defining a pupil, and a lens capsule behind the iris, the apparatus comprising:
   a frame having a front and rear, a first portion and a second portion, the frame reconfigurable between (i) a first collapsed state for being inserted through an incision in a cornea and (ii) a second operative state for being operatively connected to an iris,
   the first frame portion configured to be generally residing within a plane in the second operative state, the first frame portion having the form of a closed loop,
   the second frame portion in the second operative state configured to exert a pressure upon the iris at at least a first location that is spaced from the plane to maintain the pupil in an enlarged state with the frame operatively connected to the iris, the second frame portion connected with the first frame portion by at least one arm, the at least one arm extending from the first frame portion, and the second frame portion located at a cantilevered end of the at least one arm.

2. The surgical apparatus as recited in claim 1 wherein the first frame portion has a plurality of sides and the second frame portion has a plurality of iris engagement members, wherein each one of the iris engagement members is connected to one of the sides by an arm.

3. The surgical apparatus as recited in claim 1 wherein with frame in the second operative state, the arm is configured to deflect inward toward a front-to-rear axis of the frame.

4. The surgical apparatus as recited in claim 1 wherein with frame in the second operative state, the arm is configured to deflect in a direction substantially parallel to the plane.

5. The surgical apparatus as recited in claim 1 wherein the first frame portion has a plurality of sides of a first length and the second frame portion has a plurality of iris engagement members, wherein each one of the iris engagement members is connected to one of the sides by an arm, each arm having a second length that is greater than one half of the first length.

6. The surgical apparatus as recited in claim 1 wherein the first frame portion has a plurality of sides and the second frame portion has a plurality of iris engagement members, wherein each one of the iris engagement members is connected to one of the sides by an arm to locate each iris engagement member at a corner of two adjacent sides of the first frame portion.

7. The surgical apparatus as recited in claim 1 wherein with the frame in the second operative state the first frame portion generally has the form of a polygon.

8. The surgical apparatus as recited in claim 1 wherein with the frame in the second operative state the first frame portion generally has the form of a rectangle.

9. The surgical apparatus as recited in claim 1 wherein with the frame operatively connected and in the second operative state, the frame is configured to exert a pressure upon the iris at a location that is spaced rearwardly of the plane.

10. The surgical apparatus as recited in claim 1 wherein with the frame operatively connected and in the second operative state, the frame is configured to exert a pressure upon the iris at a location that is spaced forwardly of the plane.

11. The surgical apparatus as recited in claim 1 wherein the second frame portion comprises a plurality of channels spaced apart generally along a front-to-rear axis for receiving part of an iris and configured to exert a pressure upon the iris that maintains the pupil in an enlarged state.

12. The surgical apparatus as recited in claim 11 wherein at least two of the plurality of channels are configured to exert a different pressure upon the iris that maintains the pupil in an enlarged state with the frame operatively connected to an iris and in the second operative state.

13. The surgical apparatus as recited in claim 11 wherein the plurality of channels increase in size in a forward direction along the front-to-rear axis.

14. A method of using a surgical apparatus for assisting the performance of a procedure on an eye, the eye having a front and rear, a cornea, an iris defining a pupil, and a lens capsule behind the iris, the method comprising the steps of:
   a) obtaining a surgical apparatus in accordance with claim 1;
   b) inserting the frame in the first collapsed state through an incision in a cornea; and
   c) thereafter operatively connecting the second frame portion with an iris with the frame in the second operative state such that the at least one arm deflects to exert a pressure upon the iris that maintains the pupil in an enlarged state.

* * * * *